United States Patent
Liu et al.

(10) Patent No.: US 11,337,931 B2
(45) Date of Patent: May 24, 2022

(54) NANOPARTICLE DELIVERY SYSTEM FOR DISEASES ASSOCIATED WITH MAJOR BASEMENT MEMBRANE COMPONENTS OF BLOOD VESSELS ACCESSIBLE FROM BLOOD STREAM

(71) Applicant: University of South Florida, Tampa, FL (US)

(72) Inventors: Ruisheng Liu, Tampa, FL (US); Samuel A. Wickline, Temple Terrace, FL (US); Jin Wei, Tampa, FL (US); Hua Pan, Tampa, FL (US); Jie Zhang, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 16/950,327

(22) Filed: Nov. 17, 2020

(65) Prior Publication Data
US 2021/0069119 A1   Mar. 11, 2021

Related U.S. Application Data

(63) Continuation of application No. PCT/US2019/034890, filed on May 31, 2019.
(Continued)

(51) Int. Cl.
*A61K 9/51* (2006.01)
*A61K 47/62* (2017.01)
(Continued)

(52) U.S. Cl.
CPC .......... *A61K 9/5123* (2013.01); *A61K 9/5169* (2013.01); *A61K 31/436* (2013.01);
(Continued)

(58) Field of Classification Search
CPC .. A61K 9/5123; A61K 9/5169; A61K 31/436; A61K 31/5377; A61K 31/573;
(Continued)

(56) References Cited

U.S. PATENT DOCUMENTS

| 9,808,500 B2 | 11/2017 | Wickline et al. | |
| 2008/0175792 A1* | 7/2008 | Lanza | A61P 43/00 424/9.32 |

(Continued)

FOREIGN PATENT DOCUMENTS

WO    2017066349 A1    4/2017

OTHER PUBLICATIONS

Fredman, Gabrielle et al. Targeted nanoparticles containing the proresolving peptide Ac2-26 protect against advanced atherosclerosis in hypercholesterolemic mice. Science Translational Medicine, Feb. 18, 2015; vol. 7, Issue 275, pp. 275ra20. DOI: 10.1126/scitranslmed.aaa1065.
(Continued)

*Primary Examiner* — Gollamudi S Kishore
(74) *Attorney, Agent, or Firm* — Smith & Hopen, P.A.; Michele L. Lawson

(57) ABSTRACT

A targeting nanoparticle composition and method of treatment for diseases associated with major basement membrane components of blood vessels accessible from blood stream is presented. The composition includes pegylated perfluorocarbon nanoparticles having a targeting ligand attached that targets the basement membrane components, specifically collagen IV. The targeted nanoparticles may contain at least one pharmaceutically active agent capable of treating a glomerular disease such as lupus nephritis.

15 Claims, 10 Drawing Sheets

Specification includes a Sequence Listing.

Related U.S. Application Data

(60) Provisional application No. 62/678,673, filed on May 31, 2018.

(51) Int. Cl.
*A61K 31/436* (2006.01)
*A61K 31/5377* (2006.01)
*A61K 31/573* (2006.01)
*A61K 31/675* (2006.01)

(52) U.S. Cl.
CPC ........ *A61K 31/5377* (2013.01); *A61K 31/573* (2013.01); *A61K 31/675* (2013.01); *A61K 47/62* (2017.08)

(58) Field of Classification Search
CPC .. A61K 31/675; A61K 47/62; A61K 47/6925; A61K 9/513; A61P 9/00; C07K 7/06
See application file for complete search history.

(56) References Cited

U.S. PATENT DOCUMENTS

| | | |
|---|---|---|
| 2011/0104069 A1 | 5/2011 | Xu et al. |
| 2013/0302821 A1* | 11/2013 | Sakamoto .......... G01N 33/6893 435/7.4 |
| 2015/0306254 A1* | 10/2015 | Holers ............... A61K 49/0058 424/9.6 |
| 2016/0022835 A1 | 1/2016 | Farokhzad et al. |

OTHER PUBLICATIONS

International Search Report and Written Opinion issued by the International Searching Authority dated Sep. 11, 2019 for corresponding international patent application No. PCT/US2019/034890.

International Preliminary Report on Patentability issued by the International Bureau dated Dec. 10, 2020 for corresponding international patent application No. PCT/US2019/034890.

Chan, Juliana et al., Spatiotemporal controlled delivery of nanoparticles to injured vasculature, PNAS, Feb. 2, 2010, vol. 107, No. 5, pp. 2213-2218. DOI: 10.1073/pnas.0914585107.

Chen, Junjie et al., Perfluorocarbon nanoparticles for physiological and molecular imaging and therapy, Nov. 2013, 20(6): 466-78. DOI: 10.1053/jackd.2013.08.004.

* cited by examiner

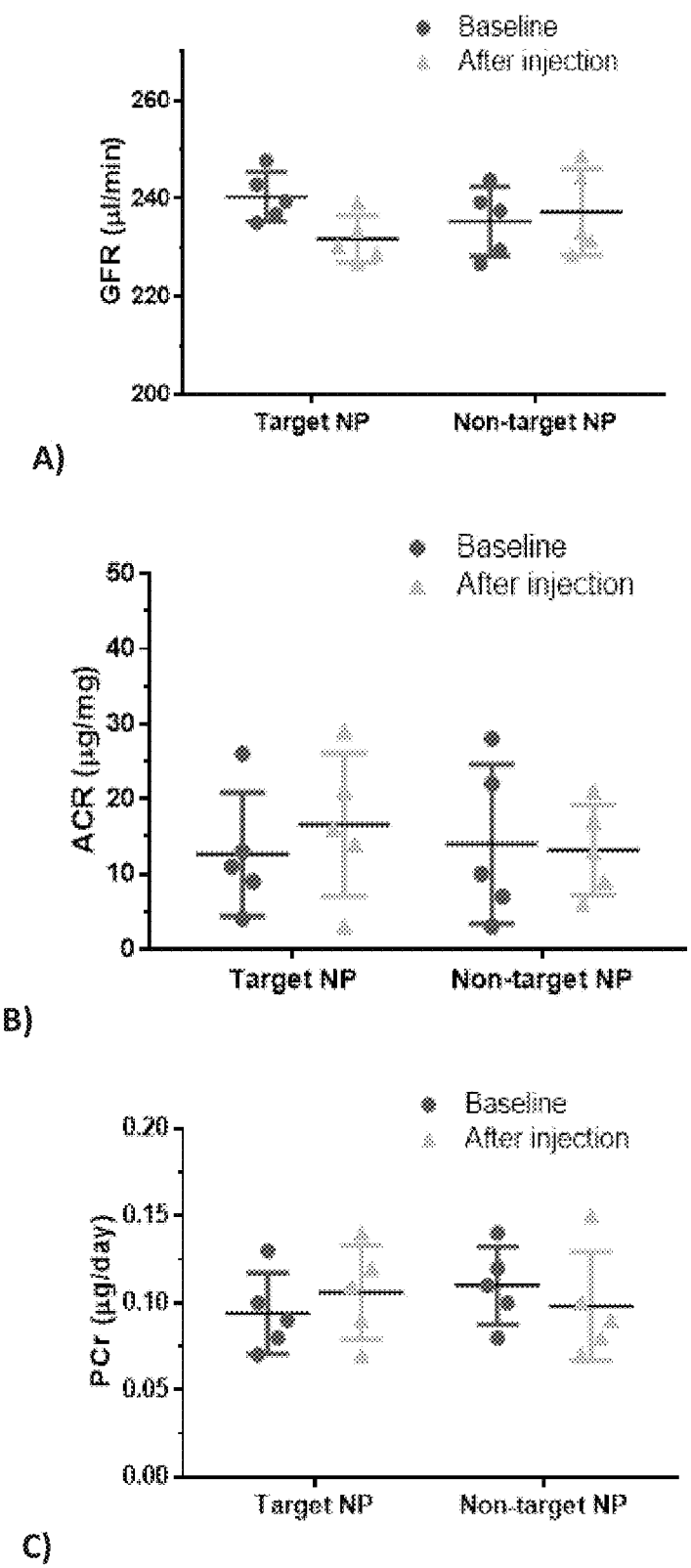
FIG. 6A-C

D)

|  | Body weight (g) | Kidney weight (g) | Blood pressure (mmHg) | Renal blood flow (ml/min) |
|---|---|---|---|---|
| Targeted NP | 27.6±2.1 | 0.146±0.006 | 88±3.6 | 0.85±0.07 |
| Non-targeted NP | 26.9±1.8 | 0.148±0.005 | 91±4.1 | 0.79±0.05 |

FIG. 6D

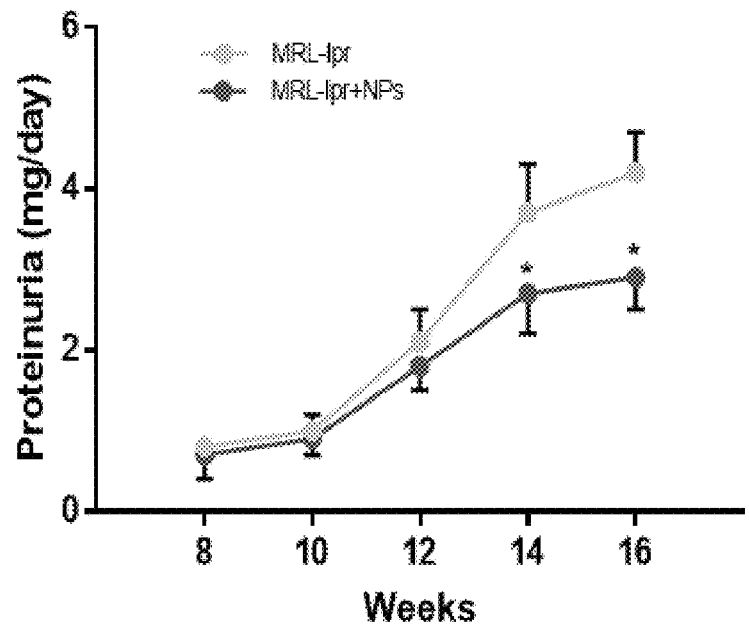
A)
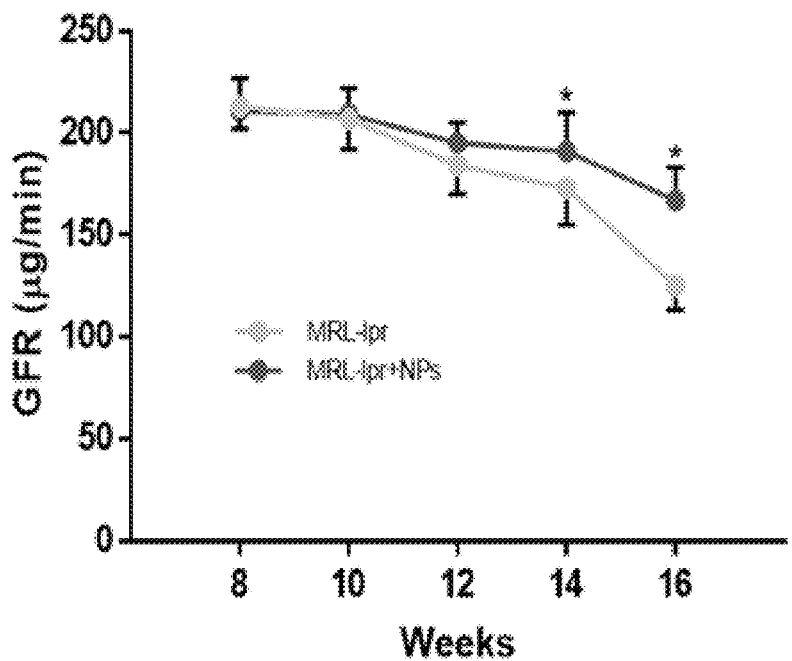
B)
FIG. 7A-B

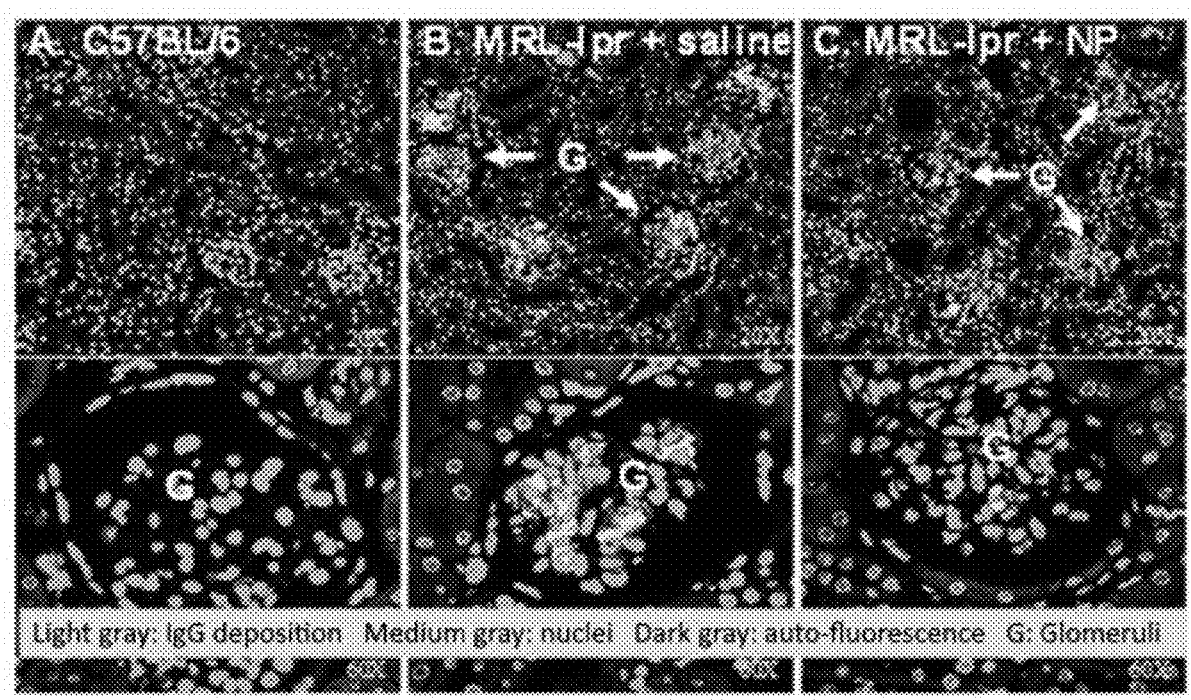
FIG. 8A-C

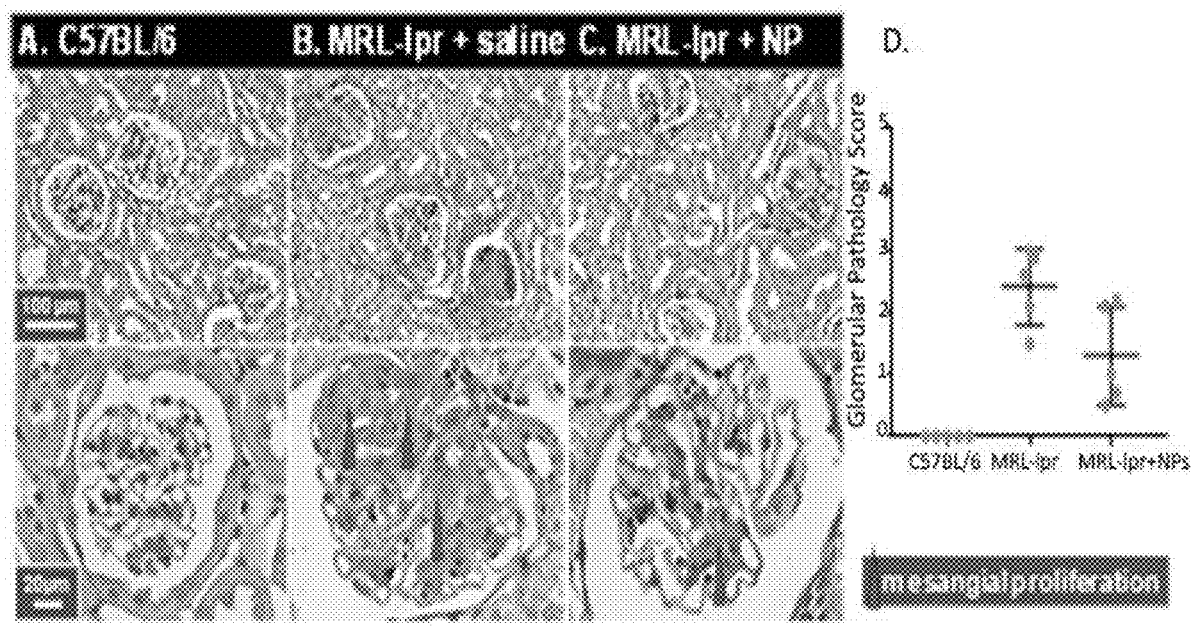
FIG. 9A-D

NANOPARTICLE DELIVERY SYSTEM FOR DISEASES ASSOCIATED WITH MAJOR BASEMENT MEMBRANE COMPONENTS OF BLOOD VESSELS ACCESSIBLE FROM BLOOD STREAM

CROSS REFERENCE TO RELATED APPLICATIONS

This application is a continuation of and claims priority to International Patent Application No. PCT/US2019/034890, entitled "Nanoparticle Delivery System for Diseases Associated with Major Basement Membrane Components of Blood Vessels Accessible from Blood Stream", filed May 31, 2019 which claims priority to U.S. Provisional Patent Application Ser. No. 62/678,673, entitled "Nanoparticle Delivery System for Diseases Associated with Major Basement Membrane Components of Blood Vessels Accessible from Blood Stream", filed May 31, 2018, the contents of which are hereby incorporated by reference into this disclosure.

GOVERNMENT SUPPORT STATEMENT

This invention was made with Government support under Grant Nos. DK098582, DK099276, HL137987, DK102691, AR067491, and HL073646 awarded by the National Institutes of Health. The government has certain rights in the invention.

FIELD OF THE INVENTION

This invention relates to treatment of diseases associated with basement membrane components in blood vessels. More specifically, the present invention relates to nanoparticle delivery systems related to treating such diseases.

BACKGROUND OF THE INVENTION

The vascular basement membrane of blood vessels is comprised of collagen IV and laminin linked by other additional extracellular matrix proteins. Collagen IV is highly conserved among mammals. Collagen IV is a heterotrimer made up of two $\alpha 1$ and one $\alpha 2$ chains that wind around each other to form a long and rigid 400 nm triple helix. The stiff triple helical structure in conjunction with covalent cross-linking between collagen IV molecules gives basement membranes mechanical resistance to tensile forces and is critical to basement membrane function. In certain diseases, inflammation or injury may expose the vascular basement membrane of the blood vessels, such as in atherosclerosis. A fenestrated epithelium is present in the basement membrane of the blood vessels of the kidneys which allows for direct contact with blood. The inventors found that by targeting major basement membrane components with targeting nanoparticles containing a pharmaceutically active agent, they could directly target the inflammation or injury to the blood vessels or directly target the kidney itself for a site-specific administration of drug.

Atherosclerosis and Hypertension

Atherosclerosis-induced cardiac complications represent the number one cause of morbidity and mortality globally. Regardless of the great advancement of modern medicine over the past two decades, the absolute deaths caused by atherosclerosis-induced heart diseases are raising.

Atherosclerosis causes chronic inflammation and tissue injury to blood vessel by the buildup of plaques within the blood vessel. The vascular basement membrane is exposed at these sites of inflammation and injury. Fredman found that by administering controlled release nanoparticles containing peptide Ac2-26 that targeted collagen IV of the vascular basement membrane, advanced atherosclerotic lesions were stabilized. (Fredman 2015).

Hypertension causes thickening and splitting of the basement membrane thus leaving the basement membrane exposed. Targeting components of the vascular basement membrane, such as collagen IV, with pharmaceutically active agents has potential to be a site-specific treatment for hypertension.

Kidney Diseases

In the glomerular capillaries, the endothelium is fenestrated with pores of about 100 to 200 nm in diameter, which means the glomerular basement membrane has direct contact with blood in circulation. The fenestrated endothelium of the glomerular capillaries allows for targeted delivery of pharmaceutically active agents directly to the kidney tissue.

Glomerulonephritis, such as lupus nephritis and IgA nephritis, is one of the leading causes for chronic kidney disease (CKD) and end-stage renal failure (ESRD). Glomerulonephritis usually requires aggressive anti-inflammatory and immunosuppressive therapy with medications like glucocorticoids, which unfortunately, are associated with severe systemic side effects. Therefore, development of new strategies which minimize the side effects while maintaining high therapeutic efficiency is essential.

Systemic lupus erythematosus (SLE) is a systemic autoimmune disease. Lupus nephritis is the renal involvement in SLE and exhibits a wide variety of symptoms from asymptomatic proteinuria to end-stage renal disease. Lupus nephritis affects many different compartments in the kidney, tissues including glomerular capillaries, GBM, mesangium, podocytes, proximal tubules and the surrounding interstitium.

As one of the most threatening manifestations of the disease, lupus nephritis is present in about three quarters of patients and significantly increases the morbidity and mortality of SLE patients. Lupus nephritis can affect any structural component with any degree of intensity, but glomeruli are the target structure in most patients. It is estimated that about 1.5 million Americans have SLE with an incidence of about 16,000 new cases per year. Lupus nephritis requires aggressive immunosuppressive therapy, however, unfortunately most of these medications are associated with severe side effects. Therefore, development of new targeted treatment strategies is essential.

Accordingly, what is needed is an improved nano-delivery system with broad applications for addressing a variety of unmet medical needs, including atherosclerosis, hypertension, and kidney diseases. However, in view of the art considered as a whole at the time the present invention was made, it was not obvious to those of ordinary skill in the field of this invention how the shortcomings of the prior art could be overcome.

SUMMARY OF THE INVENTION

The inventors have developed a novel delivery system using novel PFC nanoparticles, formed by coupling base PFC nanoparticles with a collagen IV targeting peptide, that selectively target kidney glomeruli by binding to collagen IV of the glomerular basement membrane. The targeted PFC nanoparticles may be loaded with drugs such as prednisone, mycophenolate mofetil (MMF), or rapamycin. This glomerular-specific delivery system is able to provide local therapeutics with minimal side effects.

In an embodiment, a targeting nanoparticle composition or nanoparticle delivery system is presented comprising: at least one perfluorocarbon targeted nanoparticle having a targeting ligand covalently conjugated thereto wherein the targeting ligand is a peptide targeting collagen IV, such as the peptide having 100% homology to SEQ ID NO: 1, and a pharmaceutically active agent contained within the at least one targeting nanoparticle wherein the pharmaceutically active agent is capable of treating a glomerular disease such as lupus nephritis. The targeting nanoparticle composition may further comprise a pharmaceutically acceptable carrier. The targeted nanoparticles may target collagen IV on the glomerular basement membrane. The pharmaceutically active agent may be selected from the group consisting of cyclophosphamide, prednisolone, prednisone, mycophenolate mofetil (MMF), rapamycin and combinations thereof.

In a further embodiment, a method of treating a disease associated with major basement membrane components of blood vessels in a patient in need thereof is presented comprising: providing a targeting nanoparticle composition comprising at least one perfluorocarbon targeted nanoparticle having a targeting ligand covalently conjugated thereto wherein the targeting ligand is a peptide targeting collagen IV having 100% homology to SEQ ID NO: 1; a pharmaceutically active agent contained within the at least one targeted nanoparticle wherein the pharmaceutically active agent is capable of treating a disease associated with major basement membrane components of blood vessels; and a pharmaceutically acceptable carrier; and administering the targeted nanoparticle composition parenterally to the patient in need thereof.

The disease associated with major basement membrane components of blood vessels may be selected from the group consisting of glomerular diseases, atherosclerosis, and hypertension. In some embodiments, the disease associated with major basement membrane components is a glomerular disease such as lupus nephritis.

In a further embodiment, a kit for treating a disease associated with major basement membrane components of blood vessels in a patient in need thereof is presented comprising: a targeting nanoparticle composition comprising at least one perfluorocarbon targeted nanoparticle having a targeting ligand covalently conjugated thereto wherein the targeting ligand is a peptide targeting collagen IV having 100% homology to SEQ ID NO: 1; a pharmaceutically active agent contained within the at least one targeted nanoparticle wherein the pharmaceutically active agent is capable of treating a glomerular disease; and a pharmaceutically acceptable carrier; and printed instructions for administering the targeting nanoparticle composition to the patient in need thereof.

In some embodiments, the pharmaceutically active agent may be selected from the group consisting of cyclophosphamide, prednisolone, prednisone, mycophenolate mofetil (MMF), rapamycin and combinations thereof.

BRIEF DESCRIPTION OF THE DRAWINGS

For a fuller understanding of the invention, reference should be made to the following detailed description, taken in connection with the accompanying drawings, in which:

FIG. 6A-C are a series of images depicting the evaluation of the biosafety of the collagen IV targeted nanoparticles on C57 mice. A) graph depicting GFR measurement before and after injection of therapeutic NPs; B) graph depicting proteinuria measurement before and after injection of therapeutic NPs; C) graph depicting measurement of plasma creatine before and after injection of therapeutic NPs. As shown in the images, none of the renal function parameters were significantly changed after injection of the novel therapeutic NPs.

FIG. 6D is a table comparing body weight, kidney weight, renal blood flow and renal blood pressure between control mice and mice receiving injection of therapeutic NPs. As shown in the table, none of the renal function parameters were significantly changed after injection of the novel therapeutic NPs.

FIG. 7A-B are a series of graphs depicting A) lupus mice receiving therapeutic NPs exhibited a lower level of urinary protein excretion as compared to controls; and B) lupus mice receiving therapeutic NPs exhibited better preservation of GFR as measured by the clearance of plasma FITC-inulin as compared to controls.

FIG. 8A-C are a series of images depicting IgG depositions in glomeruli visualized with confocal microscope. (A) No IgG deposition was detected in the kidney of normal C57BL/6 mice; (B) A significant amount of IgG deposition was detected in the glomeruli of control MRL-lpr mice treated with saline; (C) Treatment with prednisone loaded Col4-PFC-NP apparently decreased the glomeruli IgG deposition in the MRL-lpr mice.

FIG. 9A-D are a series of images depicting the effects of Col4-PFC-NP treatment on kidney histology. (A) C57BL/6 mice exhibit normal kidney histology; (B) MRL-lpr mice treated with saline exhibit severe kidney injury, especially mesangial proliferation; (C) The kidney injury was significantly improved in MRL-lpr mice treated with prednisone loaded Col4-PFC-NP (n=5/group, * p<0.05); (D) graph depicting the glomerular pathology score for each group of mice.

DETAILED DESCRIPTION OF THE PREFERRED EMBODIMENT

Figure 1:
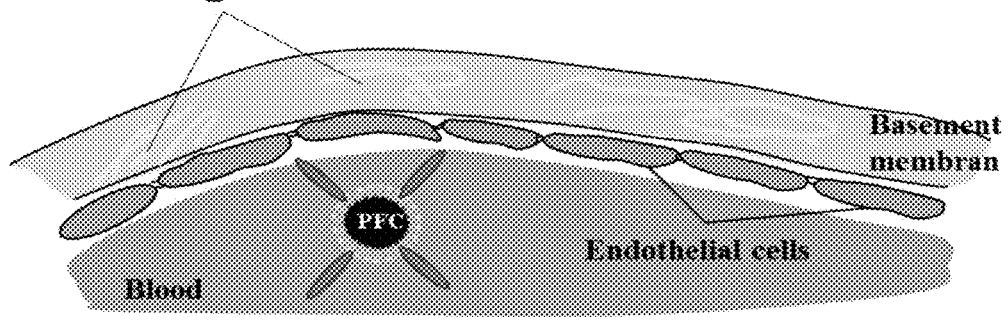
FIG. 1 is a series of images illustrating the difference between vasculatures. The image on the left depicts vasculatures of the blood vessels in which the endothelium contains cells having tight junctions. In contrast, the image on the right depicts glomerular capillaries in which the junctions between the endothelial cells are wider.
Figure 1:
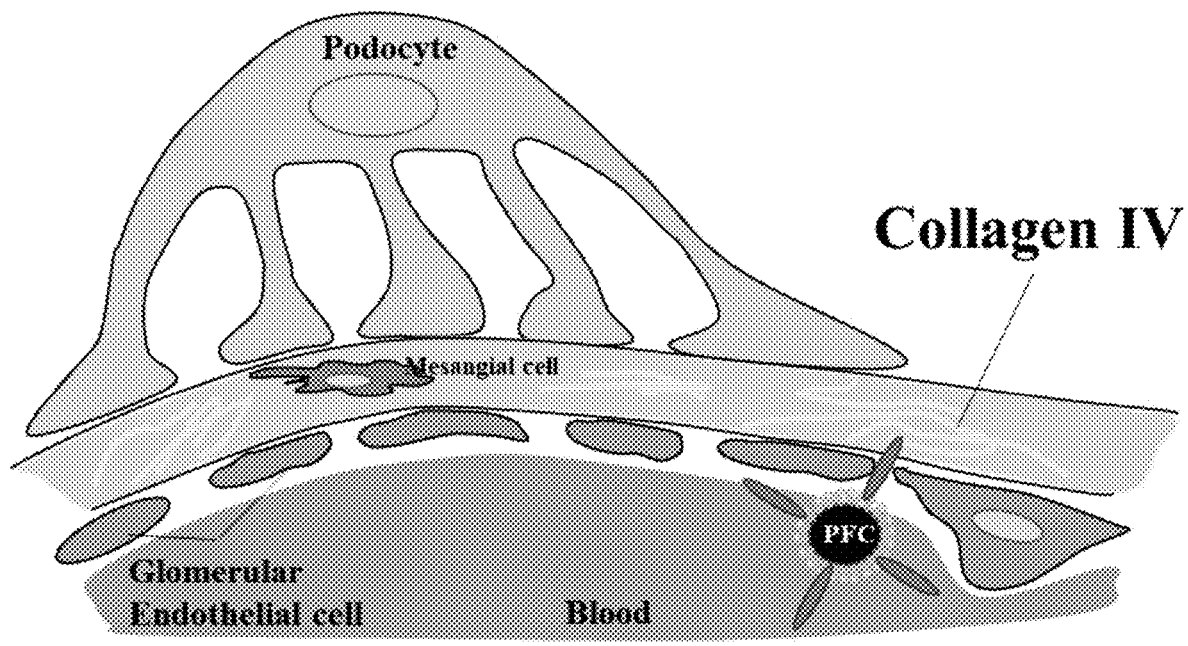

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supersedes any disclosure of an incorporated publication to the extent there is a contradiction.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose. Where particular values are described in the application and claims, unless otherwise stated, the term "about" meaning within an acceptable error range for the particular value should be assumed. As used herein, the term "about" refers to ±10% of the numerical.

As used in this specification and the appended claims, the singular forms "a", "an", and "the" include plural references unless the content clearly dictates otherwise. As used in this specification and the appended claims, the term "or" is generally employed in its sense including "and/or" unless the context clearly dictates otherwise.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace elements and pharmaceutically acceptable carriers. "Consisting of" shall mean excluding more than trace elements of other components or steps.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

The terms "pharmaceutically active agent", "drugs", "compounds" and "pharmaceutical compositions" are used interchangeably herein to refer to a molecule, a group of molecules, a complex or substance that is administered to a subject for diagnostic, therapeutic, preventative, medical, or veterinary purposes and includes drugs and vaccines. Included are externally and internally administered topical, localized and systemic human and animal pharmaceuticals, treatments, remedies, nutraceuticals, cosmeceuticals, biologicals, and diagnostics, including preparations useful in clinical and veterinary screening, prevention, prophylaxis, healing, wellness, detection, imaging, diagnosis, therapy, surgery, monitoring, and the like.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pa., Mack Publishing Company, 19$^{th}$ ed.) describes formulations which can be used in connection with the subject invention.

For ease of administration, the subject compounds may be formulated into various pharmaceutical forms. As appropriate compositions there may be cited all compositions usually employed for systemically administering drugs. These pharmaceutical compositions are desirably in unitary dosage form suitable, preferably, for administration by parenteral injection. For example, in preparing the compositions in parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules often represent the most advantageous oral dosage unit form, in which case solid pharmaceutical carriers are obviously employed.

"Patient" is used to describe a vertebrate animal, preferably a human, to whom treatment is administered, including prophylactic treatment with the compositions of the present invention. Vertebrate animals include mammals such as humans, primates, canines, felines, bovines, porcines, equines, ayes, ruminants, etc. "Patient" is used interchangeably with "subject" herein.

"Therapeutically effective amount" for purposes herein is thus determined by such considerations as are known in the art. A therapeutically effective amount of the at least one targeted nanoparticle containing at least one pharmaceutically active agent is that amount necessary to provide a therapeutically effective result in vivo. The amount of pharmaceutically active agent must be effective to achieve a response, including but not limited to total prevention of (e.g., protection against) and to improved survival rate or more rapid recovery, or improvement or elimination of symptoms associated with diseases related to major basement membrane components of blood vessels or elimination of progression of diseases related to major basement membrane components of blood vessels or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

"Administration" or "administering" is used to describe the process in which at least one targeted nanoparticle containing at least one pharmaceutically active agent of the present invention is delivered to a patient. The composition may be administered in various ways including parenteral (referring to intravenous and intraarterial and other appropriate parenteral routes), percutaneous, oral, rectal, among others. Each of these conditions may be readily treated using other administration routes of targeted nanoparticles to treat a disease or condition.

The amount of the pharmaceutically active agent in the pharmaceutical composition will depend on absorption, distribution, metabolism, and excretion rates of the drug as well as other factors known to those of skill in the art. Dosage values may also vary with the severity of the condition to be alleviated. The compounds may be administered once or may be divided and administered over intervals of time. It is to be understood that administration may be adjusted according to individual need and professional judgment of a person administrating or supervising the administration of the compounds used in the present invention. The dose of the compounds administered to a subject may vary with the particular composition, the method of administration, and the particular disorder being treated. The dose should be sufficient to affect a desirable response, such as a therapeutic or prophylactic response against a particular disorder or condition. It is contemplated that one of ordinary skill in the art can determine and administer the appropriate dosage of compounds disclosed in the current invention according to the foregoing considerations.

Dosing frequency for the composition includes, but is not limited to, at least about once every three weeks, once every two weeks, once a week, twice a week, three times a week, four times a week, five times a week, six times a week, or daily. In some embodiments, the interval between each administration is less than about a week, such as less than about any of 6, 5, 4, 3, 2, or 1 day. In some embodiments, the interval between each administration is constant. For example, the administration can be carried out daily, every two days, every three days, every four days, every five days, or weekly. In some embodiments, the administration can be carried out twice daily, three times daily, or more frequent. Administration can also be continuous and adjusted to maintaining a level of the compound within any desired and specified range.

The administration of the composition can be extended over an extended period of time, such as from about a month or shorter up to about three years or longer. For example, the dosing regimen can be extended over a period of any of about 2, 3, 4, 5, 6, 7, 8, 9, 10, 11, 12, 18, 24, 30, and 36 months. In some embodiments, there is no break in the dosing schedule. In some embodiments, the interval between each administration is no more than about a week.

"Treatment" or "treating" as used herein refers to any of: the alleviation, amelioration, elimination and/or stabilization of a symptom, as well as delay in progression of a symptom of a particular disorder.

"Glomerular disease" as used herein refers to a disease which affects kidney function by damaging the glomeruli. Glomerular diseases may be caused directly by an infection or drug toxicity or may be systemic such as in diabetes or lupus. Broadly, glomerular disease refers to diseases causing glomerulonephritis and/or glomerulosclerosis. Diseases causing glomerular disease include, but are not limited to, autoimmune diseases such as systemic lupus erythematosus (SLE) which causes lupus nephritis, Goodpasture syndrome, IgA nephropathy; Alport syndrome; infections such as acute post-streptococcal glomerulonephritis (PSGN), bacterial endocarditis, and human immune deficiency virus (HIV); sclerosis such as that caused by diabetic nephropathy and focal segmental glomerulosclerosis (FSGS); membranous nephropathy; minimal change disease (MCD); chronic kidney disease (CKD); acute renal failure (ARF); and end stage renal failure (ESRF).

"Nanoparticles" (NPs) as used herein refers to a particle or structure which is biocompatible with and sufficiently resistant to chemical and/or physical destruction by the environment of such use so that a sufficient number of the nanoparticles remain substantially intact after delivery to the site of application or treatment and whose size is in the nanometer range. For the purposes of the present invention, a nanoparticle typically ranges between about 1 nm to about 1000 nm, preferably between about 50 nm and about 500 nm, more preferably between about 50 nm and about 350 nm, more preferably between about 100 nm and about 250 nm. In some embodiments, particularly those used in treatment of glomerular diseases, the nanoparticles are perfluorocarbon (PFC) nanoparticles which comprise a hydrophobic PFC core surrounded by a lipid surfactant monolayer.

"Targeted nanoparticles" as used herein refers to nanoparticles having a targeting ligand attached thereto. In some embodiments, the nanoparticles are perfluorocarbon nanoparticles and the targeting ligand targets collagen IV.

"Targeting ligand" as used herein refers to a peptide, aptamer, antibody, protein, carbohydrate, vitamin, or organic small molecule capable of being linked to a nanoparticle and having an affinity for a specific binding partner or receptor. The targeting ligand is preferably selective as opposed to non-selective. Attachment of the targeting ligand to the nanoparticle can be either covalent conjugation or non-covalent association. In some embodiments, the targeting ligand is a peptide, specifically the peptide KLWVLPK (SEQ ID NO: 1) having affinity for collagen IV of a basement membrane. While this peptide was experimentally used herein, other targeting ligands having affinity for collagen IV of a basement membrane are contemplated.

"Peptide" as used herein refers to a series of amino acid residues that are connected to one another typically by peptide bonds between the alpha-amino and carbonyl groups of the adjacent amino acids. The term peptide includes oligopeptides and polypeptides and as such, a "peptide" can be between about 2-40 amino acids in length.

"Therapeutic nanoparticles" as used herein refers to targeted nanoparticles containing a pharmaceutically active agent.

"Targeting nanoparticle composition" as used herein refers to at least one therapeutic nanoparticle, optionally suspended in a pharmaceutically acceptable carrier. The targeting nanoparticle composition of the instant invention is used to treat diseases associated with major basement membrane components of blood vessels. In some embodiments, the targeting nanoparticle composition is used to treat a glomerular disease.

"Composition" as used herein refers to a product comprising the specified ingredients in the specified amounts, as well as any product which results, directly or indirectly, from combination of the specified ingredients in the specified amounts.

"Disease associated with major basement membrane components of blood vessels" as used herein refers to diseases in which injury or inflammation results in exposure of the vascular basement membrane and diseases of the kidney. Examples of diseases associated with major basement membrane components of blood vessels include, but are not limited to, glomerular diseases; atherosclerosis; hypertension including idiopathic pulmonary hypertension (IPAH); chronic obstructive pulmonary disease (COPD); diabetes; and lupus.

Figure 2:
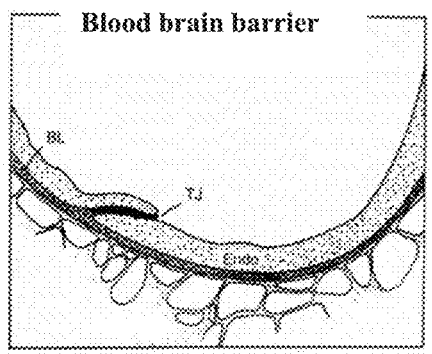
FIG. 2 is a series of images depicting the difference in vasculatures of the blood brain barrier as compared to a kidney glomerulus.
Figure 2:
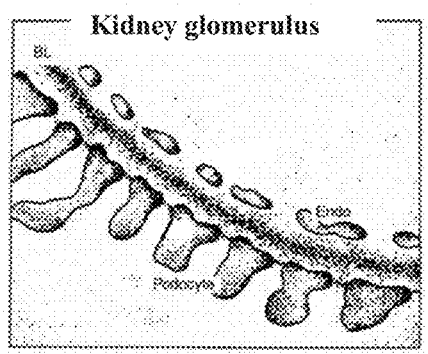
Figure 2:
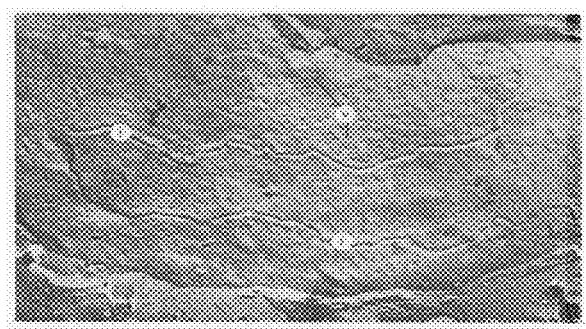
Figure 2:
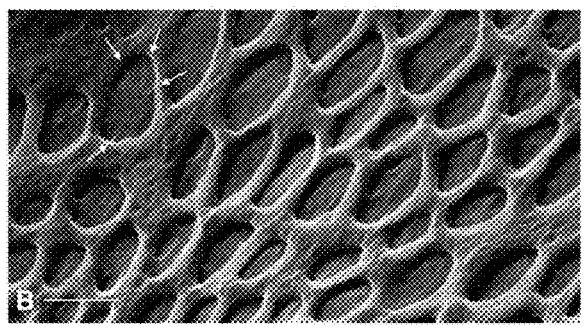

In most vasculatures, including artery, vein and capillary, the endothelium is continuous, meaning the basement membrane is completely covered by endothelial cells with tight junction. However, in the glomerular capillaries, the endothelium is fenestrated with pores of about 100 to 200 nm in diameter, which allows the glomerular basement membrane to have direct contact with blood in circulation. (FIGS. 1 and 2). The fenestrated endothelium of the glomerular capillaries allows for targeted delivery of pharmaceutically active agents directly to the kidney tissue.

Perfluorocarbon (PFC) nanoparticles (NPs) comprise a hydrophobic PFC core surrounded by a lipid surfactant monolayer and are a class of clinically approved blood-substitutes with no reports of nephrotoxic effects. With a nominal size of between about 150-250 nm, PFC nanoparticles in circulation are limited primarily to intravascular spaces unless the integrity of endothelial barriers is compromised. Due to their nominal size, PFC NP are not filtered through the glomeruli but rather are removed from circulation primarily by the reticuloendothelial system with the PFC component being vaporized through respiration. (Chen 2013). The blood clearance half-life of PFC NP ranges between about 3 to about 42 hours depending on the preparation method. (Chen 2013).

As disclosed by Chen, PFCs are typically emulsified into a nanoparticle form with a surfactant coating for stabilization and functionalization. An exemplary PFC NP emulsion typically comprises about 40% (v/v) PFOB, 2% (w/v) safflower oil, 2% (w/v) of surfactant commixture, 1.7% (w/v) glycerin, and water balance to give a final formulation having a principally liquid PFC core encapsulated by a lipid monolayer and having a diameter between about 150-250 nm with a variable surface charge between about −40 to +20 mV, depending on the types of phospholipids and surfactants used to construct it. (Chen 2013).

The inventors previously demonstrated that PFC deposited in inflamed tissues can be quantified at sparse concentrations (picomolar) with non-invasive fluorine-19 ($^{19}$F) magnetic resonance imaging (MRI), thereby allowing non-invasive confirmation of tissue homing and targeting.

Collagen IV is found exclusively in the basement membrane and forms an amorphous polygonal matrix. Chan synthesized 60 nm nanoparticles having a hydrophobic drug-eluting core, a hydrophilic polymeric shell and a lipid monolayer. The nanoparticles had a peptide targeting collagen IV conjugated to the nanoparticle via a C-terminal linker. The nanoparticles contained paclitaxel and it was found that targeted delivery could be achieved to injured rat arteries. (Chan 2010).

The inventors have developed a novel delivery system using novel PFC nanoparticles, formed by coupling base PFC nanoparticles with a collagen IV targeting peptide, that selectively target kidney glomeruli by binding to collagen IV of the glomerular basement membrane. The targeted PFC nanoparticles may be loaded with drugs such as prednisone, mycophenolate mofetil (MMF), or rapamycin. This glomerular-specific delivery system is able to provide local therapeutics with minimal side effects.

The glomerulus-targeted therapeutic PFC nanoparticles exhibits strong translational significance and offers potent site-specific treatments for lupus nephritis patients with minimized systemic side effects. Furthermore, because lupus nephritis affects many different compartments in the kidney, tissues including glomerular capillaries, GBM, mesangium, podocytes, proximal tubules and the surrounding interstitium, can be improved after treatment with the therapeutic PFC nanoparticles. The use of glomerular targeted therapeutic PFC nanoparticles allows delivery of drugs that are therapeutically active but cannot be administered systemically in sufficient doses over long intervals of time due to adverse side effects.

In certain embodiments, the current invention enables perfluorocarbon nanoparticles to target basement membrane components. This integrated delivery system could not only serve as diagnostic surrogates by using multiple imaging modalities, such as MRI and PET, but also deliver a variety of pharmaceutically active agents, including, but not limited to, small molecule drugs, antibodies, peptides, small RNA, double stranded DNA, mRNA, and plasma. Specifically, targeting ligands to major basement membrane components of blood vessels are covalently conjugated on the pegylated perfluorocarbon nanoparticles, with or without drug loading, either through covalent conjugation or non-covalent association, or both. The current system can serve a dual purpose of identifying high risk patient populations through non-invasive imaging and also of delivering the proper amount of a drug to the proper place at the right time.

The following non-limiting examples illustrate the glomerular-specific targeting nanoparticle composition with perfluorocarbon nanoparticles.

Example 1—Preparation of Nanoparticles

Glomerulonephritis and lupus nephritis usually require aggressive anti-inflammation and immunosuppressive therapy, which unfortunately, are associated with severe side effects. Therefore, development of new treatment strategies which minimize the side effects while maintaining high therapeutic efficiency is essential.

Perfluorocarbon (PFC) nanoparticles (NPs), having a nominal size of about 100 to about 250 nm, are primarily limited to the intravascular space unless the integrity of the endothelial barrier is compromised. Glomerular basement membrane (GBM) is the only site where collagen IV (Col4) has direct contact with blood via fenestrated capillary endothelium. As such, it is unexpected that PFC NPs could target Col4 in the GBM.

The inventors designed novel collagen IV-targeted PFC nanoparticles by coupling PFC nanoparticles with amine-carboxyl to a collagen IV targeting ligand, which selectively target kidney glomeruli by binding to collagen IV of the glomerular basement membrane. Formation of the PFC nanoparticles occurs by the following method. Briefly, a lipid/surfactant co-mixture of 99 mol % egg lecithin, 1 mol % 1,2-distearoyl-sn-glycero-3-phosphoethanolamine-N-[amino(polyethylene glycol)-2000] (ammonium salt), and DSPE-PEG(2000) Amine, (Avanti Polar Lipids, Piscataway, N.J.) were dissolved in a volume of methanol:chloroform (1:3 in volume). Solvent was evaporated under reduced pressure to produce a lipid film, which was dried in a 50° C. vacuum oven overnight to obtain the surfactant. The surfactant (2.0%, w/v), perfluorocarbon (20%, w/v) (Gateway Specialty Chemicals, St Peters, Mo.), and distilled, deionized water were then blended and emulsified at 20,000 PSI for four minutes in an ice bath (S110 Microfluidics emulsifier, Microfluidics, Newton, Mass.) to form the perfluorocarbon nanoparticles.

Amine-carboxyl coupling was employed to functionalize the perfluorocarbon nanoparticles containing DSPE-PEG (2000) amine with collagen IV targeting peptide, KLWVLPK (SEQ ID NO: 1). After one hour of mixing of a 1 mL emulsion with 10 mg collagen IV targeting peptide, 2 mg of EDCI (1-[3-(Dimethylamino)propyl]-3-ethylcarbodiimide methiodide) was added for overnight coupling. Excess collagen IV targeting peptide and EDCI was removed by dialysis (MWCO 3000-5000). Particle size and zeta potential was assessed before and after collagen IV targeting peptide conjugation by dynamic light scattering (Brookhaven Instruments Corp., Holtsville, N.Y.).

For the rhodamine labeled Col4-PFC-NP, 0.3 mol % of egg lecithin was replaced with 1,2-dipalmitoyl-sn-glycero-3-phosphoethanolamine-N-(lissamine rhodamine B sulfonyl) (ammonium salt). For non-targeted PFC nanoparticles, 1 mol % of DSPE-PEG(2000) amine was replaced with 1,2-dipalmitoyl-sn-glycero-3-phosphoethanolamine.

The collagen IV-targeted PFC nanoparticles can be loaded with different agents including, but not limited to, drug compounds, siRNA and peptides, and used as a glomeruli-specific carrier. Both hydrophobic and hydrophilic agents can be loaded into the NPs. Hydrophobic compounds may be loaded directly into the lipid membrane by dissolution. Hydrophilic agents may be complexed to phospholipids, such as DPPE, and formulated directly into the outer lipid coating of the NP.

The Col4-PFC-NP are able to achieve high local drug accumulation and efficient therapeutic effects in the glomeruli, with the concentration of drug being higher in the glomeruli than in blood circulation, but with minimum systemic side effects for glomerular diseases.

Example 2—In Vitro Testing of Targeted Nanoparticles

Col4-targeted PFC NPs were formulated by coupling PFC NPs to a Col4-targeting ligand as described in Example 1. The binding specificity and efficiency of the Col4-targeted NPs were evaluated on Col4 coated plate surfaces and in vitro with primary cultured mesangial cells.

Figure 3:
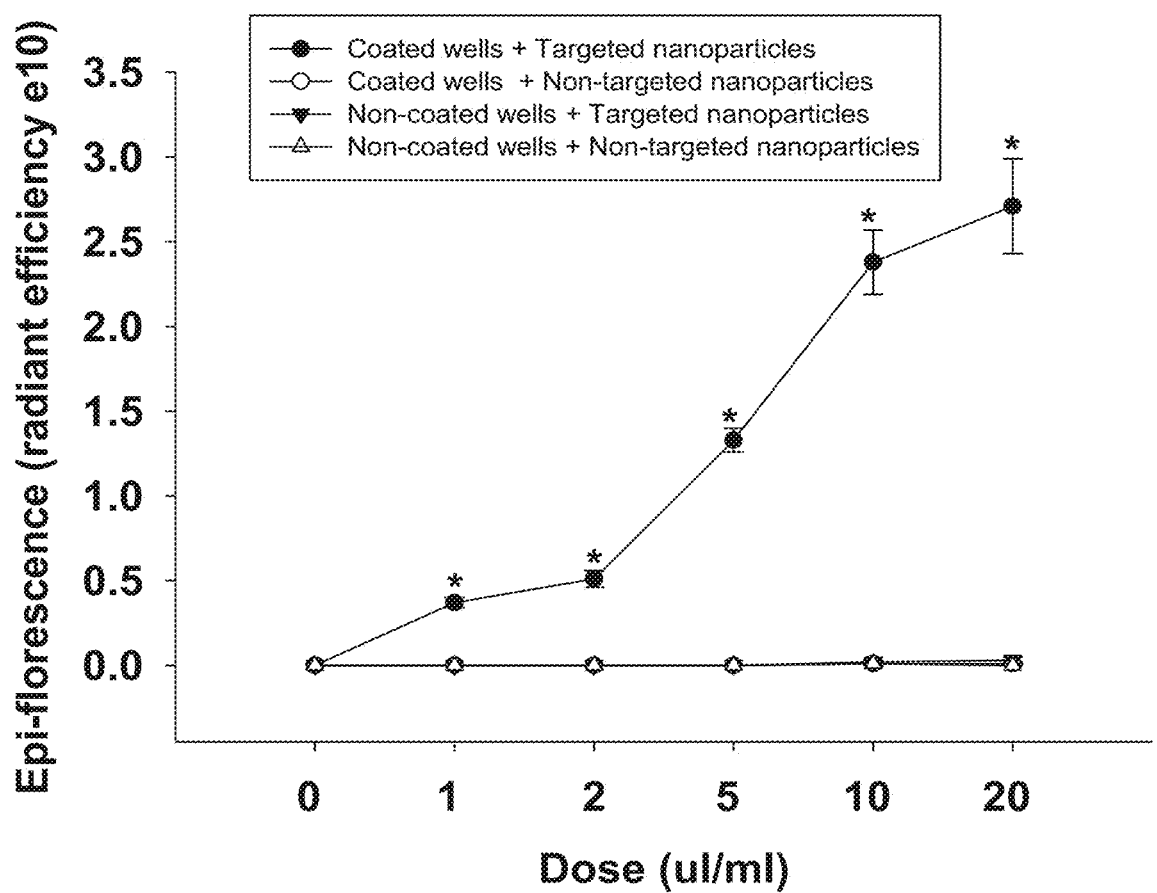
FIG. 3 is a graph depicting specific binding evaluation of the collagen IV targeted Rhodamine-labeled PFC nanoparticles on a collagen IV coated plate. Only the wells coated with collagen IV and incubated with targeted nanoparticles exhibit a dose dependent increase in fluorescent intensities.

First, rhodamine labeled Col4 targeted or non-targeted PFC NPs were applied in Col4 pre-coated 96 wells plate at stepwise doses. Briefly, a collagen IV coated plate was generated by incubating with ready to use collagen IV (Fisher Scientific) at 5 µg/cm2 in a Nunc™ 96-well plate (ThermoFisher) over night at 4° C. Wells without collagen IV coating were used for non-specific binding control. The plate was washed thoroughly 5 times with PBS, blot dried and then incubated with either collagen IV targeted or non-targeted rhodamine labeled PFC nanoparticles at 5 different concentrations (1, 2, 5, 10 and 20 µl/ml) for 2 hours at 37° C. to evaluate dose dependence of the specific binding. The binding affinity was determined by fluorescence intensity with IVIS. The wells incubated with Col4 targeted PFC NPs showed a dose dependent increase in fluorescence in radiant efficiency $e^{10}$ (0.37±0.03, 0.51±0.05, 1.33±0.07, 2.38±0.19, 2.71±0.28). Plateaus occurred at 20 µl/ml thus this amount was used as the upper threshold. Minimal non-specific binding appeared. (FIG. 3) These results indicate that the Col4 targeted PFC NPs bind to the collagen IV coated surface at dose dependent manner.

Figure 4:
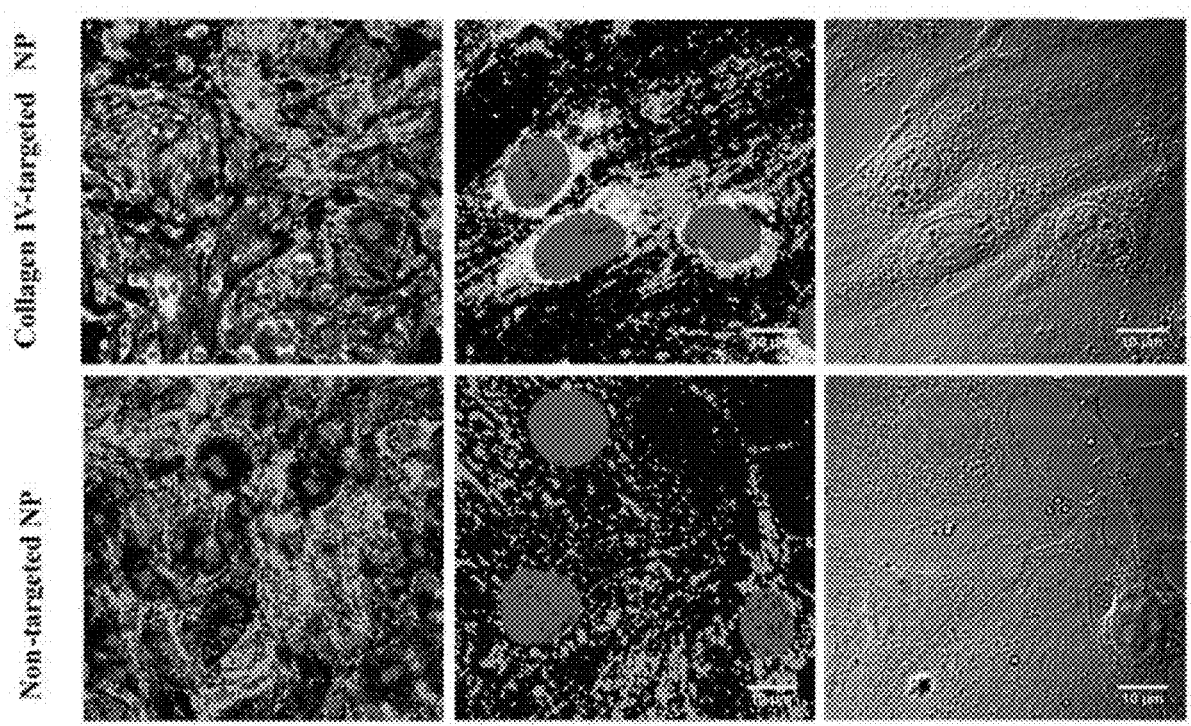
FIG. 4 is a series of images depicting specific targeting of the collagen IV targeted PFC nanoparticles on primary cultured meningeal cells. Significant uptake of nanoparticles by collagen IV is exhibited in cells incubated with targeted nanoparticles while no uptake of nanoparticles by collagen IV is exhibited in cells incubated with non-targeted nanoparticles. (medium gray—Collagen IV; light gray—nanoparticles; dark gray—nucleus)
Figure 5:
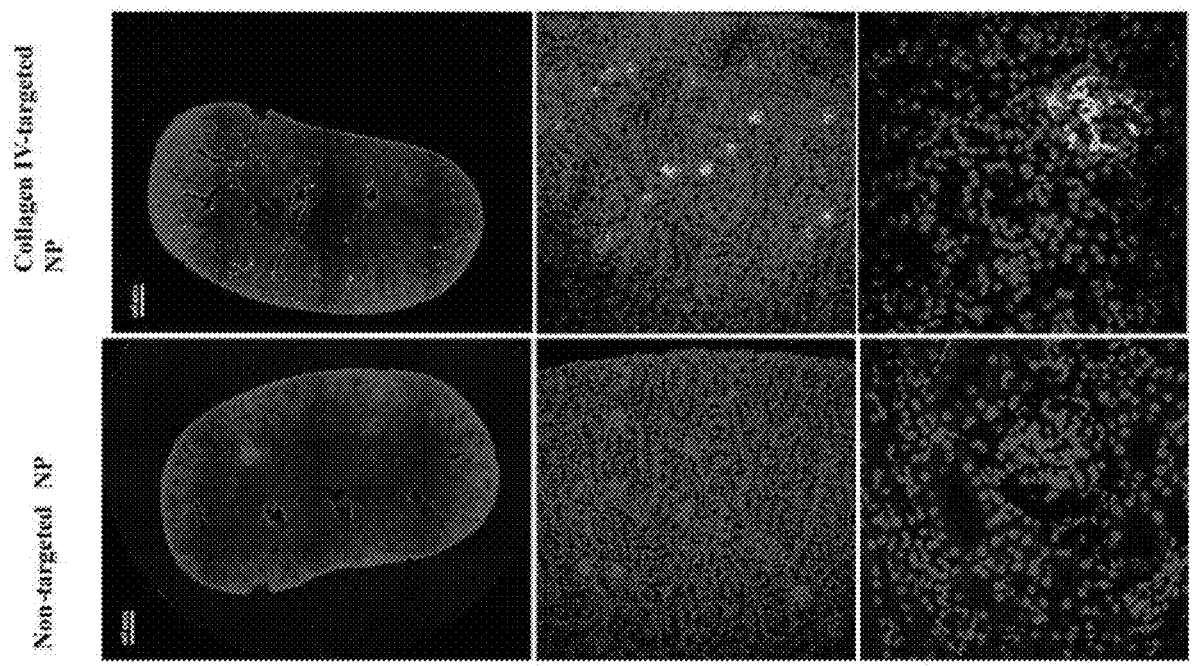
FIG. 5 is a series of images depicting kidneys from C57BL/6 mice receiving non-targeted nanoparticles or the collagen IV targeted nanoparticles. At the same confocal imaging settings, the rhodamine labeled collagen IV targeted nanoparticles were readily visualized in glomeruli of the kidneys, but non-targeted nanoparticles were barely detectable. (light grey—nanoparticles; dark grey—nucleus)

Second, primary cultured mesangial cells from C57BL/6 mice (Sciencelloline) were used to evaluate the specific targeting of Col4 targeted PFC NPs in vitro. The mesangial cells were cultured in an 8-chamber slide (Fisher Scientific) with the seeding density of 5,000 cells per well. At 48 hours post-seeding, the cells were washed thoroughly for 4 times with cell culture media followed by a single wash with PBS with $Ca^{2+}$ and $Mg^{2+}$, and then incubated with 0.2% (v/v) rhodamine labeled PFC nanoparticles with or without targeting ligands for 2 hours at 37° C. in the cell culture incubator. After this, the cells were fixed in 4% paraformaldehyde (PFA) and stained for collagen IV with secondary antibody conjugated with FITC. Significant cellular uptake of the col4 targeted NPs was visualized, while it was not detectable in the cells incubated with non-targeted NPs. (FIG. 4)

Example 3—In Vivo Testing of Targeted Nanoparticles

Col4-targeted PFC NPs were formulated by coupling PFC NPs to a Col4-targeting ligand as described in Example 1. The binding specificity and efficiency of the Col4-targeted NPs were evaluated in vivo with C57BL/6 mice.

To evaluate the targeting properties in vivo, C57BL/6 mice (male, 8 weeks old, n=6) were administered one dose of 100 µl rhodamine labeled col4 targeted or non-targeted NPs intravenously (i.v.). At 24 hours after injections, the animals were anesthetized and systemically perfused with saline. The kidneys were harvested and fixed in 4% PFA. The kidney slices were visualized with a confocal microscope. The rhodamine labeled col4 targeted NPs were selectively visualized at glomeruli in the kidney sections, while non-targeted NPs were barely detectable anywhere.

Since the distribution of NPs at glomeruli may affect filtration and permeability, renal bio-safety was evaluated by measuring GFR, plasma creatinine (PCr), proteinuria, renal blood flow and blood pressure. The blood samples (50 µL/each) were collected through the retro-orbital venous sinus and centrifuged at 8000 rpm for 5 minutes at 4° C. to separate plasma (25 µL/each). The PCr was measured by HPLC at the O'Brien Center Core of the University of Alabama at Birmingham (UAB).

The urine samples were collected in metabolic cages for 24 h. The urinary albumin concentration was measured with ELISA kit (ab108792; Abcam, Cambridge, Mass.) and the urinary creatinine concentration was also measured by HPLC at UAB. Urine albumin-to-creatinine ratio (ACR) was calculated by urinary albumin concentration over urinary creatinine concentration.

GFR in conscious mice was measured by the clearance of plasma FITC-sinistrin with a single bolus injection via retro-orbital sinus. Briefly, FITC-sinistrin solution (5.6 mg/100 g BW) was injected through the retro-orbital venous sinus, and then blood (<10 µl) was collected into heparinized capillary tubes through the tail vein at 3, 7, 10, 15, 35, 55, and 75 minutes after sinistrin injection. The blood samples were centrifuged at 8000 rpm for 5 minutes at 4° C. and plasma (1 µl) was collected from each sample. FITC-sinistrin concentration of the plasma was measured using a plate reader (Cytation3; BioTek, VT, USA) with 485-nm excitation and 538-nm emission. GFR was calculated with a GraphPad Prism 6 (GraphPad Software).

The blood pressure and renal blood flow were measured simultaneously in anesthetized mice. Briefly, the animals were anesthetized with pentobarbital (80 mg/kg, i.p.) and placed on a temperature-controlled table kept at 37° C. throughout the experiment. The trachea was cannulated (PE-50; Fisher Scientific, Hampton, N.H.) to facilitate respiration. The left femoral vein was catheterized (PE-10; Fisher Scientific, Hampton, N.H.) to infuse 1% bovine serum albumin solution (1 ml/h/100 g) and the right femoral artery was catheterized to measure blood pressure with a pressure transducer (Adinstruments, Sydney, Australia). Through a left flank incision, a flow probe was placed around the left renal artery to measure renal blood flow with an ultrasound transit-time flowmeter (TS-420; Transonic Systems Inc., Ithaca, N.Y.).

As shown in FIGS. 6A-D, none of these renal function parameters were found to be significantly changed after i.v. injection of the glomeruli-targeted NPs in C57BL/6 mice thus indicating biosafety of the administration of the Col4-PFC-NPs.

Example 4—In Vivo Therapeutic Effect of Targeted Nanoparticles

The therapeutic effect of the col4 targeted NPs loaded with prednisone for lupus nephritis was evaluated in MRL-lpr mice, an animal model of lupus nephritis with spontaneous lymphoproliferation. Collagen IV targeted nanoparticles were prepared as described in Example 1. The formulation of col4 targeted NPs loaded with prednisone were the same as the procedures described in Example 1 for col4 targeted NPs, with the exception of 5 mol % prednisone being added into the lipid film.

The prednisone loaded col4 targeted NPs (1 ml/kg) were intravenously injected in MRL-lpr mice (male, 8 weeks old, n=6) twice a week for a total of 8 weeks. Measurements of GFR and proteinuria were measured every 2 weeks. The urine samples were collected in metabolic cages for 24 h. The urinary albumin concentration was measured with ELISA kit (ab108792; Abcam, Cambridge, Mass.) and the amount of albuminuria per day was calculated.

GFR in conscious mice was measured by the clearance of plasma FITC-sinistrin with a single bolus injection via retro-orbital sinus. Briefly, FITC-sinistrin solution (5.6 mg/100 g BW) was injected through the retro-orbital venous sinus, and then blood (<10 µl) was collected into heparinized capillary tubes through the tail vein at 3, 7, 10, 15, 35, 55, and 75 minutes after sinistrin injection. The blood samples were centrifuged at 8000 rpm for 5 minutes at 4° C. and plasma (1 µl) was collected from each sample. FITC-sinistrin concentration of the plasma was measured using a plate reader (Cytation3; BioTek, VT, USA) with 485-nm excitation and 538-nm emission. GFR was calculated with a GraphPad Prism 6 (GraphPad Software).

IgG deposition and renal pathology were assessed at the conclusion of the experiment. To detect immune complex deposition in GBM, the mouse kidneys were taken at the end of experiments and snap-frozen in OCT Medium. After sectioning on a cryostat, 2-mm kidney sections were fixed with ice-cold acetone and stained with anti-IgG (ab150113; Abcam, Cambridge, Mass.). The IgG deposition was visualized with a confocal microscope and quantified by the mean fluorescence of 50 glomerular cross sections from the respective mice using the Image J software. For renal histology, the mouse kidneys were fixed in 4% paraformaldehyde for 24 h at 4° C. Paraffin embedded sections of 4 µm were stained with periodic acid-Schiff. Histopathological features of glomerular lesions were graded semi-quantitatively for severity, in a double-blinded manner according to the following criteria: grade 0, no recognizable lesion in glomeruli; grade 1, mild mesangial proliferation; grade 2, extensive mesangial proliferation; grade 3, lobulation and hyaline droplet formation; grade 4, crescent and granuloma formation and hyalinosis. The grade score for individual mice was an average of 50 glomerular cross sections from the respective mice.

Systemic lupus erythematosus is a disease of immune complex-induced microvascular injury. The deposition of immune complex, such as IgG in GBM indicates the progression of lupus nephritis. Compared with control MRL-lpr mice that were injected with saline, MRL-lpr mice receiving therapeutic NPs exhibited less glomerular deposition of IgG (142±25 vs. 193±18) evaluated by mean fluorescence intensity of immunofluorescence as shown in FIG. 8A-C.

The MRL-lpr mice receiving therapeutic NPs also exhibited decreased proteinuria (54±17 vs. 82±21 mg/dl) as shown in FIG. 7A and a better preservation of GFR as compared to control mice (157±16 vs. 118±12 ml/min) as shown in FIG. 7B. As shown in FIGS. 9A-D, MRL-lpr mice receiving therapeutic NPs exhibited reduced glomerular pathology versus control mice (1.3±0.8 vs. 2.4±0.6) evaluated by scoring 50 glomerular cross sections per kidney with periodic acid-Schiff stain.

MRL-lpr mice treated with prednisone loaded col4 targeted NPs significantly improved renal function and ameliorated kidney injury, including lower proteinuria, higher GFR, fewer IgG depositions in the glomeruli and less kidney injuries in histology compared with the control mice, indicating that these glomeruli-targeted NPs loaded with prednisone protect against the progression of lupus nephritis.

CONCLUSION

In conclusion, PFC nanoparticles were developed herein that selectively target glomeruli by binding to Col4 of GBM. These nanoparticles provide a novel tool to administer precise therapeutics with minimum side effects for lupus nephritis and other glomerular diseases. These nanoparticles also make it possible to deliver drugs in a site-specific manner that are therapeutically active but cannot be administered systemically in sufficient doses over long intervals of time due to adverse side effects.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

The disclosures of all publications cited above are expressly incorporated herein by reference, each in its entirety, to the same extent as if each were incorporated by reference individually.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

It is also to be understood that the following claims are intended to cover all of the generic and specific features of the invention herein described, and all statements of the scope of the invention that, as a matter of language, might be said to fall therebetween. Now that the invention has been described,

---

What is claimed is:

1. A targeting nanoparticle composition comprising:
   at least one perfluorocarbon targeted nanoparticle having a targeting ligand covalently conjugated thereto via amine-carboxyl coupling wherein the targeting ligand is a peptide targeting collagen IV; and
   a pharmaceutically active agent contained within the at least one perfluorocarbon targeted nanoparticle wherein the pharmaceutically active agent is capable of treating a glomerular disease;
   wherein the at least one perfluorocarbon targeted nanoparticle is generated by the process comprising
      dissolving a lipid/surfactant co-mixture comprising DSPE-PEG(2000) amine in a volume of solvent;
      evaporating the solvent to produce a lipid film;
      drying the lipid film to obtain the surfactant;
      emulsifying the surfactant, a perfluorocarbon, and water in an ice bath to form at least one perfluorocarbon nanoparticle; and
      coupling the peptide targeting collagen IV to the at least one perfluorocarbon nanoparticle via amine-carboxyl coupling by mixing an emulsion containing the at least one perfluorocarbon nanoparticle containing DSPE-PEG(2000) amine with the peptide targeting collagen IV and 1-[3-(Dimethylamino)propyl]-3-ethylcarbodiimide methiodide (EDCI) to form the at least one perfluorocarbon targeted nanoparticle.

2. The targeting nanoparticle composition of claim 1, further comprising a pharmaceutically acceptable carrier.

3. The targeting nanoparticle composition of claim 1, wherein the targeted nanoparticles target collagen IV on the glomerular basement membrane.

4. The targeting nanoparticle composition of claim 3, wherein the pharmaceutically active agent is selected from the group consisting of cyclophosphamide, prednisolone, prednisone, mycophenolate mofetil (MMF), rapamycin and combinations thereof.

5. The targeting nanoparticle composition of claim 1, wherein the glomerular disease is lupus nephritis.

6. The targeting nanoparticle composition of claim 1, wherein the peptide targeting collagen IV has 100% homology to SEQ ID NO: 1.

7. A method of treating a disease associated with major basement membrane components of blood vessels in a patient in need thereof comprising:
   providing a targeting nanoparticle composition wherein the targeting nanoparticle composition comprising:
      at least one perfluorocarbon targeted nanoparticle having a targeting ligand covalently conjugated thereto via amine-carboxyl coupling wherein the targeting ligand is a peptide targeting collagen IV;
      a pharmaceutically active agent contained within the at least one perfluorocarbon targeted nanoparticle wherein the pharmaceutically active agent is capable of treating a disease associated with major basement membrane components of blood vessels; and
      a pharmaceutically acceptable carrier;
      wherein the at least one perfluorocarbon targeted nanoparticle is generated by the process comprising
         dissolving a lipid/surfactant co-mixture comprising DSPE-PEG(2000) amine in a volume of solvent;
         evaporating the solvent to produce a lipid film;
         drying the lipid film to obtain the surfactant;
         emulsifying the surfactant, a perfluorocarbon, and water in an ice bath to form at least one perfluorocarbon nanoparticle; and
         coupling the peptide targeting collagen IV to the at least one perfluorocarbon nanoparticle via amine-carboxyl coupling by mixing an emulsion containing the at least one perfluorocarbon nanoparticle containing DSPE-PEG(2000) amine with the peptide targeting collagen IV and 1-[3-(Dimethylamino)propyl]-3-ethylcarbodiimide methiodide (EDCI) to form the at least one perfluorocarbon targeted nanoparticle; and
   administering the targeted nanoparticle composition to the patient in need thereof.

8. The method of claim 7, wherein the disease associated with major basement membrane components of blood vessels is selected from the group consisting of glomerular diseases, atherosclerosis, and hypertension.

9. The method of claim 8, wherein the disease associated with major basement membrane components is glomerular disease.

10. The method of claim 9, wherein the glomerular disease is lupus nephritis.

11. The method of claim 7, wherein the targeting nanoparticle composition is administered parenterally.

12. The method of claim 7, wherein the peptide targeting collagen IV has 100% homology to SEQ ID NO: 1.

13. A kit for treating a disease associated with major basement membrane components of blood vessels in a patient in need thereof comprising:
   a targeting nanoparticle composition wherein the targeting nanoparticle composition comprising:
      at least one perfluorocarbon targeted nanoparticle having a targeting ligand covalently conjugated thereto via amine-carboxyl coupling wherein the targeting ligand is a peptide targeting collagen IV;
      a pharmaceutically active agent contained within the at least one perfluorocarbon targeted nanoparticle wherein the pharmaceutically active agent is capable of treating a glomerular disease; and
      a pharmaceutically acceptable carrier;
      wherein the at least one perfluorocarbon targeted nanoparticle is generated by the process comprising
         dissolving a lipid/surfactant co-mixture comprising DSPE-PEG(2000) amine in a volume of solvent;
         evaporating the solvent to produce a lipid film;
         drying the lipid film to obtain the surfactant;
         emulsifying the surfactant, a perfluorocarbon, and water in an ice bath to form at least one perfluorocarbon nanoparticle; and
         coupling the peptide targeting collagen IV to the at least one perfluorocarbon nanoparticle via amine-carboxyl coupling by mixing an emulsion containing the at least one perfluorocarbon nanoparticle containing DSPE-PEG(2000) amine with the peptide targeting collagen IV and 1-[3-(Dimethylamino)propyl]-3-ethylcarbodiimide methiodide (EDCI) to form the at least one perfluorocarbon targeted nanoparticle; and
   printed instructions for administering the targeting nanoparticle composition to the patient in need thereof.

14. The kit of claim 13, wherein the peptide targeting collagen IV has 100% homology to SEQ ID NO: 1.

15. The kit of claim 13, wherein the pharmaceutically active agent is selected from the group consisting of cyclophosphamide, prednisolone, prednisone, mycophenolate mofetil (MMF), rapamycin and combinations thereof.

* * * * *

SEQUENCE LISTING

```
<160> NUMBER OF SEQ ID NOS: 1

<210> SEQ ID NO 1
<211> LENGTH: 7
<212> TYPE: PRT
<213> ORGANISM: artificial sequence
<220> FEATURE:
<223> OTHER INFORMATION: Collagen 4 Targeting Ligand

<400> SEQUENCE: 1

Lys Leu Trp Val Leu Pro Lys
1               5
```